(12) United States Patent
Mariau et al.

(10) Patent No.: US 10,722,460 B2
(45) Date of Patent: Jul. 28, 2020

(54) PHARMACEUTICAL COMPOSITIONS OF IL-2

(71) Applicant: ILTOO PHARMA, Paris (FR)

(72) Inventors: Jérémie Mariau, Fontenay sous Bois (FR); Michel Thiry, Trooz (BE)

(73) Assignee: ILTOO Pharma, Paris (FR)

( * ) Notice: Subject to any disclaimer, the term of this patent is extended or adjusted under 35 U.S.C. 154(b) by 25 days.

(21) Appl. No.: 15/770,066

(22) PCT Filed: Oct. 20, 2016

(86) PCT No.: PCT/EP2016/075204
§ 371 (c)(1),
(2) Date: Apr. 20, 2018

(87) PCT Pub. No.: WO2017/068031
PCT Pub. Date: Apr. 27, 2017

(65) Prior Publication Data
US 2018/0303754 A1  Oct. 25, 2018

(30) Foreign Application Priority Data
Oct. 22, 2015 (EP) .................................. 15306696

(51) Int. Cl.
| | | |
|---|---|---|
| *A61K 38/20* | (2006.01) |
| *A61K 9/08* | (2006.01) |
| *A61K 9/00* | (2006.01) |
| *A61K 47/20* | (2006.01) |
| *A61K 9/19* | (2006.01) |
| *A61K 47/00* | (2006.01) |
| *A61K 47/02* | (2006.01) |
| *A61J 1/05* | (2006.01) |

(52) U.S. Cl.
CPC .............. *A61K 9/08* (2013.01); *A61K 9/0019* (2013.01); *A61K 9/19* (2013.01); *A61K 38/2013* (2013.01); *A61K 47/00* (2013.01); *A61K 47/02* (2013.01); *A61K 47/20* (2013.01); *A61J 1/05* (2013.01)

(58) Field of Classification Search
CPC ................................................. A61K 38/2013
See application file for complete search history.

(56) References Cited

U.S. PATENT DOCUMENTS

| 4,530,787 A | 7/1985 | Shaked et al. |
| 4,752,585 A | 6/1988 | Koths et al. |

FOREIGN PATENT DOCUMENTS

| AU | 2006200923 A1 | 3/2006 |
| EP | 1688146 A1 | 8/2006 |
| WO | WO 85/04328 A1 | 10/1985 |

OTHER PUBLICATIONS

Stratagene Catalog, 1988, p. 39.*

* cited by examiner

*Primary Examiner* — Prema M Mertz
(74) *Attorney, Agent, or Firm* — Polsinelli PC

(57) ABSTRACT

The invention relates to a liquid pharmaceutical composition of Il-2 and its use in the treatment of auto-immune and inflammatory disorders. Methods for preparing said composition and delivery devices filled with said composition are also described.

17 Claims, No Drawings

PHARMACEUTICAL COMPOSITIONS OF IL-2

This Application is a national stage filing under 35 U.S.C. 371 of International Patent Application Serial No. PCT/EP2016/075204, filed Oct. 20, 2016, which claims priority to European application number 15306696.4, filed Oct. 22, 2015, the entire disclosure of each of which is incorporated by reference herein in its entirety.

FIELD OF THE INVENTION

The invention relates to new pharmaceutical compositions comprising interleukin-2 (IL-2) and their uses in the treatment of autoimmune-related or inflammatory disorders.

TECHNOLOGICAL BACKGROUND

Interleukin-2 is a cytokine that was originally described as permitting the activation and proliferation of T lymphocytes. It has been used clinically for the stimulation of effector immune response in certain cancers and infectious disease. Interleukin-2 was approved under the tradename Proleukin® in 1998 for the treatment of metastatic renal cell carcinoma. The posology of Proleukin® includes the intermittent administration of high dosage of IL-2, typically $42.10^6$ UI per 8 h for a patient of 70 kg by continuous infusion or by daily subcutaneous injection for 5 days, which can be repeated several times after a free-treatment period.

Recently, it was shown that interleukin-2 is essential for the survival and activation of Tregs. At doses 10 to 100 times lower than Proleukin®, IL-2 does not stimulate immunity but restores self-tolerance by specifically activating cells that regulate immunity, regulatory T cells (Treg). IL-2 therefore exerts selective biological effect on the Treg/Teff balance, a key immunological driver of immune homeostasis. Such a property paves the way for the use IL2 in the treatment of autoimmune diseases and inflammatory disorders (AIDs) inherently due to a Treg insufficiency (Klatzmann & Abbas, Nature Reviews Immunology, 2015, 15, 283-294). IL-2 is currently being investigated at low dose in the treatment of several autoimmune and inflammatory diseases such as type-1 diabetes.

Interleukin-2 is susceptible to degradation in the presence of water and oxygen. According to the prior art, Interleukin-2 may undergo chemical degradation and physical instability in solution. Accordingly, the development of lyophilized formulations was initiated to avoid such degradation reactions. In that respect, several studies were performed in order to identify stabilizers to improve the stability of IL-2 in lyophilized formulation. For instance, Hora et al. (Develop. Biol. Standard, 1991, vol 74, 295-306) describe the use of amorphous excipients such as amino-acids, non-ionic surfactant, hydroxypropyl-β-cyclodextrin or serum albumin as lyophilization stabilizers for formulating interleukin-2. In order to produce stable standards of cytokines such as Il-2, the World Health Organization (WHO) recommends freeze-drying the protein in the presence of appropriate excipient and buffer agent and to store the resulting formulation in dry condition, at low temperature, and under inert atmosphere (Mire-Sluis at al., Journal of immunological methods, 1998, 216, 103-116). Noteworthy, Proleukin®, for the treatment metastatic renal cell carcinoma, is marketed as a lyophilized composition comprising interleukin-2, mannitol, sodium dodecyl sulphate and sodium dihydrogen phosphate dihydrate, which is packaged in vial under inert condition and must be stored at 2° C. to 8° C. Mannitol is present as a lyophilization stabilizer. Proleukin® is to be reconstituted with water for injection. Once reconstituted, Proleukin® should be used immediately and, in any case, within 24 h after reconstitution (see for instance the Summary of Product Characteristics for Proleukin® in United Kingdom, Jan. 20, 2015, Novartis Pharmaceuticals UK Ltd).

Such lyophilized formulations are not appropriate for self-administration and long-term treatments because the formulations have to be reconstituted and can only be stored upon short period of time once reconstituted.

There is thus a need for alternative pharmaceutical compositions of interleukin-2.

SUMMARY OF THE INVENTION

The invention relates to a liquid pharmaceutical composition suitable for injection to a patient, consisting essentially of interleukin-2 at a concentration of 0.1 to 20 million IU/mL, a buffering agent, a surfactant, and an optional excipient preferably selected from antioxidants, osmolarity adjusting agents, and preservatives, in water. The interleukin-2 may be present at a concentration of 2 to 12 MIU/mL, preferably from 4 to 10 MUI/mL. In certain embodiments, the surfactant is an anionic surfactant, such as sodium dodecyl sulfate (SDS) and lithium dodecyl sulfate. The surfactant may be present at a concentration of about 0.05 to 0.5 mg/mL. The weight ratio of the surfactant to interleukin-2 is typically from 0.04 to 5, for instance from 0.1 to 3.0.

The liquid pharmaceutical composition of the invention is preferably obtained from a non-lyophilized interleukin-2.

In some embodiments, the liquid pharmaceutical composition is devoid of mannitol and/or albumin.

The interleukin-2 may be a recombinant human interleukin-2 or variants thereof, such as aldesleukin.

In other or additional embodiments, the liquid pharmaceutical composition consists essentially of
  interleukin-2 at a dose of 2 to 12 MIU/mL, such as from 4 to 10 MUI/mL,
  sodium dodecyl sulfate (SDS) at a concentration of about 0.05 to 0.5 mg/mL,
  a buffer selected from monobasic sodium phosphate, dibasic sodium phosphate and combinations thereof present at a concentration ranging from 5 mM to 25 mM,
  optionally an osmolarity adjusting agent such as NaCl, and
  water.

The liquid pharmaceutical composition of the invention is preferably stable at 5° C. for a period of at least 6 months.

In some alternate or additional embodiments, the liquid pharmaceutical composition of the invention may have at least one of the following features:
  the pH of the composition is from 7.1 to 7.8, preferably at pH 7.5±0.2,
  the buffering agent is a phosphate buffer,
  interleukin-2 is aldesleukin
  the liquid pharmaceutical composition is suitable for a packaging in a delivery device for injection such as a syringe or a pen,
  The pharmaceutical composition is devoid of any lyophilization stabilizer, The present invention also relates to the use of the liquid pharmaceutical composition of the invention for an administration by subcutaneous route. Typically, the liquid pharmaceutical composition of the invention can be used in the treatment or the prevention of an auto-immune, immune related or inflammatory disorder. In such uses, said composition is typically administered by subcutaneous route in an amount equivalent to a dose of interleukin-2 of 0.1 MIU to 3 MIU.

A further object of the invention is a method for preparing a liquid pharmaceutical composition as described above which comprises the steps of:
a. providing a concentrated solution of purified interleukin-2, preferably containing more than 20 mUI/mg of interleukin-2
b. formulating said concentrated solution of purified interleukin-2 by adding one or several excipients, so as to obtain said liquid pharmaceutical composition of interleukin-2.
c. Optionally packaging the liquid pharmaceutical composition into a vial, a cartridge or a delivery device for injection, such as a syringe or a pen.

The invention also relates to a pharmaceutical kit comprising a vial or a cartridge filled with said liquid composition, and means for subcutaneous injection such as syringe(s), needle(s) and/or autoinjector device. A further object of the invention is a delivery system for injection, preferably for subcutaneous injection, filled with the liquid composition as defined above.

DETAILED DESCRIPTION OF THE INVENTION

The Inventors demonstrated that it is possible to prepare a liquid aqueous formulation of Interleukin-2 which is ready for injection and which can be stored several months at temperature between 2° C. and 8° C. without any significant degradation or loss of biological activity. The Inventors thus overcame prejudices by developing a highly stable aqueous pharmaceutical composition of interleukin-2 while the prior art teaches the poor stability of interleukin-2 in water and clearly leads to the development of lyophilized formulations.

The pharmaceutical composition developed by the Inventors is very simple and does not rely on the use of sophisticated and expensive excipients. The formulation contains very few excipients, typically a surfactant, a buffer agent and an optional excipient. The optional excipient may be, for instance, an antioxidant, a preservative or an osmolarity adjusting agent. The method of preparation does not require any step of lyophilization of Interleukin-2. Indeed, lyophilization of the protein is not required, and should be avoided because it might be prejudicial to the biological activity and the stability of interleukin-2 in reconstituted solution.

The liquid pharmaceutical composition of the invention comprises a low concentration of Interleukin-2, for instance from $1·10^6$ to $5·10^6$ IU/mL. The Inventors surprisingly showed that, even at these low concentrations, Il-2 may be stable in the liquid composition of the invention. The liquid pharmaceutical composition of the invention is thus particularly appropriate for use in chronic treatments. Said composition is suitable for frequent administrations and can be used in the treatment of AIDs such as type-1 diabetes, multiple sclerosis, and rheumatoid arthritis. As the pharmaceutical composition of the invention is ready for injection, said pharmaceutical composition can be conditioned in pen devices or syringes and are thus particularly adapted for self-administration.

Moreover, the liquid pharmaceutical composition of the invention is expected to produce less local side-effects such as local skin reactions (redness and/or swelling) at the site of injection as compared to Proleukin®.

At last, the method for preparing the liquid pharmaceutical composition of the invention is simpler and more rapid than those described in the prior art, because Interleukin-2 is formulated just after purification steps without any lyophilization.

Pharmaceutical Composition According to the Invention

A first object of the invention is an aqueous liquid pharmaceutical composition suitable for injection to a patient comprising from $0.1·10^6$ to $20·10^6$ IU/mL of interleukin-2.

As used herein, the term "suitable for injection" means that the liquid pharmaceutical composition can be administered by injection, preferably by intravenous, intramuscular, intradermal or subcutaneous route to the patient.

In a preferred embodiment, the liquid pharmaceutical composition of the invention is suitable for intradermal or subcutaneous injection.

Preferably, the aqueous liquid pharmaceutical composition of the invention is ready for use, in particular ready for injection. As used herein, "ready for injection" means that the liquid pharmaceutical composition can be directly administered to the patient without being subjected to any further step of formulation.

As used herein, "formulation step" refers to the addition of one or several excipients to a composition.

Preferably, the interleukin-2 present in the liquid pharmaceutical composition of the invention has not been subjected to freeze-drying (or lyophilization process). As used herein, the terms "freeze-drying" or "lyophilization" refer to a dehydration process comprising freezing a material comprising water and reducing pressure so as to allow frozen water in the material to be removed by sublimation.

For instance, Proleukin® is a solid pharmaceutical composition of interleukin-2 obtained by lyophilization.

Thus, the liquid pharmaceutical composition of the invention is preferably prepared from a non-lyophilized interleukin-2, i.e. from an interleukin-2 which has not been subjected to any lyophilization process. In a more general aspect, the liquid pharmaceutical composition of the invention can be prepared by a process of manufacturing which is devoid of a step in which interleukin-2 is freeze-dried or lyophilized, even in the presence of a lyophilization stabilizer. Suitable processes for preparing the liquid pharmaceutical composition of the invention are described further below.

As used herein, Interleukin-2 (IL-2) encompasses mammal wild type Interleukin-2, and variants thereof. Preferably, IL-2 is a human IL-2, or a variant thereof.

Active variants of IL-2 have been disclosed in the literature. Variants of the native IL-2 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide, for instance mature wild type human IL-2.

Methods for determining whether a variant IL-2 polypeptide is active are available in the art and are specifically described in the present invention. An active variant is, most preferably, a variant that stimulates Tregs.

Examples of IL-2 variants are disclosed, for instance, in EP109748, EP136489, U.S. Pat. No. 4,752,585; EP200280, or EP118,617.

IL-2 can be produced by DNA recombinant technique. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. Nos. 4,656,132; 4,748,234; 4,530,787; or U.S. Pat. No. 4,748,234, incorporated therein by reference.

Alternatively, IL-2 can be produced by chemical peptide synthesis. For instance, IL-2 can be produced by the parallel synthesis of shorter peptides that are subsequently assembled to yield the complete sequence of IL-2 with the correct disulfide bridge. A total synthesis of Interleukin-2 is illustrated for instance in Asahina et al., Angewandte Chemie International Edition, 2015, Vol. 54, Issue 28, 8226-8230, the disclosure of which being incorporated by reference herein.

In some embodiment, IL-2 is a variant having at least 80%, preferably at least 90%, 95%, 98%, 99%, sequence identity with a mature wildtype human IL-2. The variant can be glycosylated or non-glycosylated. A nucleotide sequence and an amino acid sequence of human IL-2 are disclosed, for instance, in Genbank ref 3558 or P60568, respectively.

IL-2 is commercially available, including for pharmaceutical uses, and it is authorized for use in human patients. Suitable commercial forms include, e.g.

Proleukin® (aldesleukin) is a recombinant unglycosylated des-alanyl-1, serine-125 human interleukin-2, produced in *E. coli*.

Roncoleukin® is a recombinant human IL-2 produced in yeast.

In a preferred embodiment, IL-2 is aldesleukin. Aldesleukin is the active ingredient of Proleukin®. Aldesleukin is an unglycosylated variant of mature human IL-2 comprising two amino acid modifications as compared to the sequence of mature human IL-2: the deletion of the first amino acid (alanine) and the substitution of cysteine at position 125 by serine. IL-2 for use in the present invention is preferably in essentially pure form, e.g., at a purity of 95% or more, further preferably 96, 97, 98 or 99% pure.

IL-2 for use in the present invention has typically a specific activity of 1.2 to 24 million international unit (MIU) per mg of protein, preferably from 8 to 18 MIU/mg of protein. For instance, the IL-2 present in the composition of the invention can have a specific activity of 12±3 MIU per mg of protein.

For instance, if the IL-2 has a specific activity of about 12 MIU per mg of protein, the liquid composition of the invention may comprise from about 0.008 to about 1.67 mg of said IL-2 per mL.

The biological activity of IL-2 is preferably determined by a cell-based assay performed on HT-2 cell line (clone A5E, ATCC® CRL-1841™) whose growth is dependent on IL-2. Cell growth in the presence of a range of test interleukin-2 product is compared with the growth recorded with IL-2 international standard (WHO 2nd International Standard for INTERLEUKIN 2 (Human, rDNA derived) NIBSC code: 86/500). Cell growth is measured after addition and transformation of [3-(4,5-dimethylthiazol-2-yl)-5-(3-carboxymethoxyphenyl)-2-(4-sulfophenyl)-2H-tetrazolium (inner salt, MTS) into formazan by active viable cells. Formazan concentration is then measured by spectrophotometry at 490 nm.

In some embodiments, interleukin-2 is present in the liquid composition of the invention in the form of monomers, aggregates and combinations thereof.

The liquid composition of the invention preferably consists essentially of interleukin-2 at a concentration of 0.1 to 20 million IU/mL, a buffering agent, a surfactant and an optional excipient selected from antioxidants, osmolarity adjusting agents, and preservatives in water. As used herein, "consists essentially of" means that the recited components represent more than 95% by weight of the liquid composition. In other words, the interleukin-2, the buffering agent, the surfactant, the optional excipient and water preferably account for more than 95%, for example for more than 96%, 97% 98%, 99%, 99.5% or 99.9% in weight of the total weight of the liquid composition.

The water is the carrier of the solution. Typically the water is of pharmaceutical grade.

The surfactant is present so as to promote the solubility and the stability of interleukin-2 in solution. Suitable surfactants encompass, without being limited to, $C_8$-$C_{20}$ alkylsulfate salts, certain phospholipids such as phosphatidates, cholate salts, deoxycholate salts, salts of lauroyl sarcosinate (such as sodium salt known as sarkosyl), CHAPS, CHAPSO, Triton X100, Triton X114, NP40, octyl glucoside, polyethylene glycol dodecyl ethers for instance that marketed under tradename Brij™35, polyethylene glycol hexadecyl ethers for instance that marketed under the tradename Brij™58, polyoxyethylene derivatives of sorbitan monolaurates such as Tween 20 and Tween 80, sorbitan esters such as sorbitan monostearate or sorbitan monolaurate, and combinations thereof In some embodiments, the surfactant is an anionic surfactant. Accordingly, the surfactant can be selected from $C_8$-$C_{20}$ alkylsulfate salts, lauroyl sarcosinate salts, cholate salts, deoxycholate salts and combinations thereof.

Preferred anionic surfactants according to the invention are dodecyl sulphate salts such sodium dodecyl sulphate (SDS) or lithium dodecyl sulphate. For instance the surfactant can be selected among alkali metal and alkaline-earth metal dodecyl sulphates. A preferred surfactant is SDS.

Without to be bound by any theory, the Inventors believe that the concentration of the surfactant in the solution and the weight ratio of the surfactant to IL-2 can have some impacts on the stability of interleukin-2 over time. In some embodiments, the surfactant, in particular dodecylsulfate salts such as SDS, is present at a concentration of 0.01 to 0.5 mg/mL. Without to be bound by any theory, the Applicant is of the opinion that a concentration of surfactant, in particular dodecylsulfate salts such as SDS, higher than 0.05 mg/ml may promote the stability of IL2 in solution by forming micelles. In preferred embodiment, the surfactant, preferably SDS, is present at a concentration from 0.05 to 5.0 mg/ml, for instance from 0.06, 0.07, or 0.08 to 5.0 mg/ml. The surfactant may be present at a concentration from 0.08 to 0.4 mg/ml in the liquid composition of the invention.

In additional or alternate embodiments, the weight ratio of the surfactant, preferably SDS, to interleukin-2 is from 0.01 to 5, preferably from 0.04 to 5 for instance from 0.1 to 3. For illustration, the weight ratio of surfactant to interleukin-2 may be from 0.1 to 0.4, for instance from 0.15 to 0.30 or from 1.0 to 3.0, for instance from 1.5 to 2.5.

The buffering agent can be of any type with proviso that it is appropriate to formulate interleukin-2 and adapted for injection, in particular subcutaneous injection. The buffering agent refers to acids, salt forms of acids and combination thereof. Buffering agents encompass phosphoric acid, Tris (hydroxymethyl)aminomethane hydrochloride (TRIS.HCl), 4-Morpholinepropanesulfonic acid (MOPS), 4-(2-Hydroxy-ethyl)piperazine-1-ethanesulfonic acid (HEPES), PIPES, 2,2-Bis(hydroxymethyl)-2,2',2"-nitrilotriethanol (BIS-TRIS), TRIS-glycine, Bicine, Tricine, TAPS, TAPSO, MES, citrate, borate, citrate/phosphate, bicarbonate, glutaric acid, succinic acid, salts thereof and combinations thereof.

The concentration of the buffering agent in the liquid formulation of the invention is typically from 1 mM to 100 mM, preferably from 5 mM to 25 mM, such as from 5 mM to 15 mM.

The pH of the liquid composition of the invention is preferably from 7.0 to 8.0, for instance pH 7.5±0.2. In some embodiments, the buffering agent(s) have a pKa from about to about 6.5 to 8.5, preferably from 7.0 to 8.0. Preferably, the buffering agents are salts of phosphoric acid, such as sodium, calcium or potassium salts of acid phosphoric. For instance the buffering agent is selected from sodium phosphate monobasic, sodium phosphate dibasic and combinations thereof. In other words, preferred buffers are phosphate buffers.

In preferred embodiments, the liquid pharmaceutical composition of the invention has an osmolarity suitable for subcutaneous injection. Typically the osmolarity of the composition of the invention is at least of 250 mOsm, preferably at least 330 mOsm, and in particular at least 360 mOsm.

The optional excipient may be selected from preservatives, antioxidants and combinations thereof. Preservatives encompass, without being limited to, benzalkonium chloride, benzoic acid, sorbic acid and salts thereof. Antioxidants encompass ascorbic acid, ascorbyl palmitate, tocopherol and combinations thereof. Typically the optional excipient accounts for less than 5% by weight, preferably less than 3%, 2%, 1%, and even 0.1% by weight of the total weight of the composition.

The optional excipient may be also selected among osmolarity adjusting agents. Osmolarity adjusting agents comprises pharmaceutically acceptable inorganic salts such as sodium chloride and potassium chloride and organic salts such sodium or potassium organic salts, for instance potassium or sodium citrate, aspartate or acetate. The osmolarity adjusting agent is typically added in the composition of the invention in an amount enabling to adjust the osmolarity of the composition at a value of at least 330 mOsm or at least 360 mOsm. The osmolarity is typically from 330 mOsm to 600 mOsm. NaCl is a preferred osmolarity adjusting agent according to the invention.

In some embodiments, the liquid pharmaceutical composition is devoid of any optional excipient. In some particular embodiments, the liquid pharmaceutical composition of the invention contains a osmolarity adjusting agent but is devoid of any preservative or antioxidant agents In some embodiments, the liquid pharmaceutical composition of the invention consists essentially of interleukin-2 at a concentration of 0.1 to 20 million IU/mL, a buffering agent, and a surfactant in water. In other embodiments, the liquid pharmaceutical composition of the invention consists essentially of interleukin-2 at a concentration of 0.1 to 20 million IU/mL, a buffering agent, an osmolarity adjusting agent and a surfactant in water.

As mentioned above, the interleukin-2 used for preparing the composition of the invention is preferably a non-lyophilized interleukin-2. Consequently, the presence of a lyophilization stabilizer is not required in the liquid pharmaceutical composition of the invention. As used, "a lyophilization stabilizer" or "a freeze-drying stabilizer" refers to an excipient able to protect proteins, in particular interleukin-2, from denaturation during lyophylization. Lyophilization stabilizers typically encompass sugars such as mannitol, sucrose, dextrose and trehalose, amino-acids, hydroxypropyl-β-cyclodextrin and serum albumin.

In some embodiments, the liquid composition is devoid of any lyophilization stabilizer.

In some other embodiments, the liquid composition of the invention is devoid of mannitol and/or albumin.

The Inventors demonstrated that the liquid pharmaceutical composition of the invention is stable over time. The liquid pharmaceutical composition can be stored at a temperature from 2° C.–8° C., preferably 5° C., under inert atmosphere, during at least 6 months without any significant loss of biological activity, i.e. with a decrease of the biological activity of at most 25%, preferably at most 20%, 15%, 10% or 5%. In particular, after a period of storage of 6 months at 5° C., the decrease of the biological activity of interleukin-2 in the solution is lower than 30%, preferably lower than 25% or 20%, in particular lower than 15%, 10% or 5% of the biological activity before storage. As used herein, "the liquid pharmaceutical composition is stable" means that the liquid pharmaceutical composition of the invention is stable when stored at a temperature of 5° C., under inert atmosphere, over a period of at least 6 months, even at least 12 months. In some embodiments, the liquid pharmaceutical composition may be stable when stored at a temperature from 2° C. to 8° C. and under inert atmosphere over a period of one to three years.

Noteworthy, the liquid pharmaceutical composition is stable even if Interleukin-2 is present at a low concentration, for instance at less than 12 MIU per mL, for instance from 2 to 12 MIU per mL. Stable liquid pharmaceutical compositions comprising a low amount interleukin-2 is of a high interest for a use in the chronic treatment of autoimmune and inflammatory disorders because they are convenient for packaging in delivery devices such as syringes and pens adapted for self-administration.

In some embodiments, the liquid pharmaceutical composition of the invention comprises interleukin-2 at an amount of 0.1 to 12 MIU per mL of composition, for instance from 0.1 to 10 MIU per mL or from 2 to 12 MIU per mL of composition. An amount of 0.1 to 12 MIU per mL encompasses an amount of 0.1 to 1 MIU per mL, of 1 MIU to 2 MIU per mL, of 2 MIU to 3 MIU per mL, of 3 MIU to 4 MIU per mL, 4 MIU to 5 MIU per mL, of 5 MIU to 6 MIU per mL, of 6 MIU to 7 MIU per mL, of 7 MIU to 8 MIU per mL, of 8 MIU to 9 MIU per mL, of 9 MIU to 10 MIU per mL, of 10 MIU to 11 MIU per mL, of 11 MIU to 12 MIU per mL. In preferred embodiments, the liquid pharmaceutical composition of the invention comprises interleukin-2 at an amount of 4 MIU to 10 MIU per mL, for instance at an amount of 4 MIU to 6 MIU per mL.

In some particular embodiments, the liquid pharmaceutical composition of the invention comprises interleukin-2 at an amount of 0.1 to 6 MIU per mL of composition, preferably from 0.5 to 5 MIU per mL. For instance, the amount of interleukin-2 is the composition of the invention may be 0.5 MIU per mL, 1.0 MIU per mL, 1.5 MIU per mL, 2.0 MIU per mL, 2.5 MIU per mL, 3.0 MIU per mL; 3.5 MIU per mL, 4.0 MIU per mL, 4.5 MIU per mL, or 5.0 MIU per mL.

In some particular embodiments, the liquid pharmaceutical composition of the invention comprises from 1.0 to 3.0 MIU of interleukin-2 per mL.

For example, in said embodiments, if the IL-2 has a specific activity of about 12 MIU per mg of protein, 1.0 to 3.0 MIU of interleukin-2 per mL corresponds to about 0.08 mg of IL-2 per mL to about 0.24 mg of IL-2 per mL.

In some other embodiments of the invention, the liquid pharmaceutical composition consists essentially of:
- Interleukin-2 in an amount of 1.0 to 3.0 MIU per mL, or from 2 MIU to 12 MUI per mL such as 4 MUI to 10 MUI per mL or such as 4 MUI to 6 MUI per mL
- a surfactant, preferably sodium dodecyl sulphate (SDS),
- a buffer agent, preferably selected from phosphate salts such as sodium monobasic phosphate and sodium dibasic phosphate,
- an optional excipient, preferably selected from preservatives, antioxidants and osmorality adjusting agents, and
- water As mentioned above, the surfactant, in particular SDS, may be present at an amount 0.01 to 0.50 mg/mL. Preferably SDS is present at a concentration from 0.05 to 0.5 mg/mL. In alternate or additional embodiments, the weight ratio of the surfactant, preferably SDS, to Interleukin-2 is from 0.04 to 5, more preferably from 0.1 to 3.0 for instance from 2.0 to 2.5, such as a 2.2 or from 0.10 to 0.30, such as 0.22.

In some embodiments, the liquid pharmaceutical composition consists essentially of
- Interleukin-2 in an amount of 1.0 to 3.0 MIU per mL, or from 2 MIU to 12 MUI per mL such as 4 MUI to 10 MUI per mL
- sodium dodecyl sulphate (SDS) present at a concentration of about 0.05 to 0.5 mg/mL
- a phosphate buffer,
- water, and
- optionally an osmolarity adjusting agent, preferably NaCl.

In some alternate or additional embodiments, the liquid composition of the invention is characterized by one or several of the following features:
- the liquid composition is suitable for injection to a patient
- the liquid composition consists essentially of Interleukin-2 in an amount of 2.0 to 12 MIU per mL, a surfactant, a buffer agent, a osmolarity adjusting agent and water,
- the surfactant is SDS which is present at a concentration 0.1 to 0.4 mg/mL
- the buffer agent is phosphate salts present at a total concentration from 1 mM to 100 mM, preferably from 5 mM to 25 mM
- the pH of the composition is from 7.0 to 8.0, preferably pH 7.5±0.2,
- the weight ratio of the surfactant to interleukin-2 is from 0.1 to 3.0,
- Interleukin-2 is a non-lyophilized interleukin-2
- Interleukin-2 has a specific activity of 12±3 MIU per mg of protein,
- The interleukin-2 is aldesleukin
- The pharmaceutical composition is devoid of lyophilization stabilizers, including mannitol,
- The osmolarity adjusting agent is NaCl,
- The osmolarity of the liquid composition is at least 330 mOsm, preferably at least 360 mOsm.
- The pharmaceutical composition is stable when stored at a temperature of 5° C. and under inert atmosphere over a period of at least 6 months,
- The liquid pharmaceutical composition is packaged in an injection delivery device for instance a syringe or a pen.
- The liquid pharmaceutical composition is suitable for subcutaneous administration.

In some embodiments, the liquid composition is characterized by all the above-listed features.

Method for Preparing the Liquid Pharmaceutical Composition of the Invention

The present invention also relates to a method for preparing a liquid pharmaceutical composition of interleukin-2 suitable for injection to a patient as described above, which comprises:
a. providing a concentrated solution of purified interleukin-2, and
b. formulating the concentrated solution of purified interleukin-2 by adding one or several excipients, so as to obtain said liquid pharmaceutical composition of interleukin-2.

Typically, the concentrated solution of purified interleukin-2 of step a) comprises water as carrier, and a buffer agent. Interleukin-2 is present in the concentrated solution at a concentration more than 20 MIU/mL, preferably at a concentration of at least 25 MIU, for instance from 25 MIU to 50 MIU per mL. The concentrated solution is generally at a pH from 7.0 to 8.0. The concentrated solution of purified interleukin-2 is obtained by a standard process of production of IL-2. Said standard process can comprise the recombinant production of IL-2 in a host culture and the recovery and the purification of Interleukin-2 from the host culture so as to obtain the concentrated solution of purified interleukin-2. The process used to prepare the concentrated solution of Interleukin-2 is preferably devoid of lyophilization step. In some embodiment, said process is also devoid of a step of reconstitution wherein a liquid carrier is added to a solid composition of IL-2, for instance a lyophilized composition of Interleukin-2.

In some embodiments, the concentrated solution of purified interleukin-2 can be obtained by a process comprising:
i. producing interleukin-2 in a recombinant *E. coli* culture,
ii. recovering interleukin-2 from the recombinant *E. coli* culture, and purifying interleukin-2 so as to obtained the concentrated solution of purified interleukin-2.

The production of Interleukin-2 in *E. coli* can be performed by standard methods. The recovery and the purification of interleukin-2 from *E. coli* culture can be also performed by standard methods and may include steps such as homogenization and centrifugation of *E. coli* culture, the recovery and solubilization of the inclusion bodies, refolding of the protein, one or several steps of chromatography such as size exclusion chromatography, ion-exchange chromatography, affinity chromatography, multimodal chromatography, reversed-phase chromatography, HPLC, or hydroxyapatite chromatography, one or several steps of filtration such as depth filtration, ultrafiltration, tangential ultrafiltration, nanofiltration, and reverse osmosis. The solution of purified interleukin-2 can be concentrated by ultrafiltration so as to obtain the desired concentration of Il-2 (e.g. a concentration of at least 15 MIU/mL). Before purification, IL-2 recovered from the cell culture can be subjected to a refolding step.

Alternatively, the concentrated solution of purified IL-2 can be obtained by chemical synthesis. For instance, the process for preparing said concentrated solution can comprise the production of IL-2 by peptide synthesis and the purification of said chemically-produced IL-2 so as to obtain said concentrated solution. For instance IL-2 can be prepared by parallel synthesis of shorter peptides in solid or liquid phases, preferably by solid phase method. The resulting peptides are subsequently ligated together to lead to the complete sequence of IL-2. The resulting IL-2 is then purified by standard methods such as preparative chromatography steps and refolded if needed.

Before being formulated, the concentrated solution of purified interleukin-2 can be subjected to sterilization and/or viral inactivation steps. Typically, the concentrated solution of purified interleukin-2 can be subjected to a sterile filtration. The concentrated solution of purified interleukin-2 may also comprise surfactant or other excipients such as antioxidants and preservatives.

Preferably, the concentrated solution of purified interleukin-2 consists essentially of interleukin-2 at a concentration of at least 15 MIU/mL, preferably of at least 20 MIU/mL, a buffer agent, water and optionally a surfactant. Preferred buffering agent is a phosphate buffer and a preferred surfactant is SDS.

The formulation of the concentrated solution of purified interleukin is carried out so as to obtain the desired liquid pharmaceutical composition interleukin-2. Depending on the features of the starting concentrated solution of purified interleukin-2 and the desired final pharmaceutical, step b) may comprise:
- diluting the solution so as to adjust the concentration of interleukin-2 in the range of 0.1 MIU to 20 MIU per mL, for instance from 2 MIU to 12 MIU per mL, from 4 MIU to 10 MIU per mL, from 0.1 MIU to 10 MIU per mL, or from 0.1 MIU to 6 MIU, and/or
- adding a surfactant and/or adjusting the concentration of the surfactant
- adding one or several buffer agents so as to adjust the pH between 7.0 and 8.0 and/or so as to adjust the molarity of the buffer in the solution to a value between 1 mM to 100 mM, for instance from 5 mM to 25 mM, and/or
- adding the optional excipient selected from antioxidants, preservatives, osmolarity adjusting agents and combinations thereof.

The method of the invention may further comprise a step c) of packaging. Typically, the liquid pharmaceutical composition of the invention can be packaged in a device for injection, for instance in a syringe or in a pen for injection, under inert atmosphere or modified atmosphere such as under argon or nitrogen. Alternatively, the liquid pharmaceutical can be conditioned in a vial or in cartridges under inert atmosphere. Said vial or cartridge filled with the liquid pharmaceutical composition of the invention can be packaged together with means for injection such as syringe, needle and autoinjector system. The packaging of the pharmaceutical composition for injection is preferably performed under aseptic conditions. The method of the invention may also comprise sterilization or viral inactivation steps, for instance by e-beam irradiation. Said steps can be carried out before or after the packaging, depending on the technology used. For instance, the liquid pharmaceutical composition can be subjected to a sterile filtration before packaging and/or e-beam irradiation after packaging.

In some embodiments, the method for preparing the liquid pharmaceutical composition of interleukin-2 suitable for injection to a patient as described above comprises the steps of:
i. producing interleukin-2 in a recombinant host culture, preferably *E. coli*,
ii. recovering interleukin-2 from the recombinant host culture, and purifying interleukin-2 so as to obtained a concentrated solution of purified interleukin-2,
iii. formulating the concentrated solution of purified interleukin-2 so as to obtain the liquid pharmaceutical composition of interleukin-2, and
iv. optionally packaging the liquid pharmaceutical composition of interleukin-2 in a device for injection, such as a syringe or a pen.

As mentioned above, the method of the invention is devoid of a step wherein interleukin-2 is freeze-dried.

Step iv is preferably performed in aseptic conditions.

It goes without saying that the instant invention also relates to the liquid pharmaceutical composition obtainable by such a method as well as injection device filled with said liquid pharmaceutical composition.

Uses, Therapeutic Methods, Kits and Devices According to the Invention

The present invention also relates to the use of the liquid pharmaceutical composition of interleukin-2 of the invention in the treatment or the prevention of an autoimmune, immune-related or inflammatory disorder in a subject. Preferred autoimmune, immune-related or inflammatory disorder in a subject relate to disorders associated with an insufficiency of Tregs.

Autoimmune, immune-related or inflammatory disorders include without being limited to, HCV-related vasculitis, uveitis, myositis, type I diabetes, systemic lupus erythematous, systemic vasculitis, psoriasis, allergy, asthma, Crohn's disease, Multiple Sclerosis, Rheumathoid Arthritis, atherosclerosis, autoimmune thyroid disease, neuro-degenerative diseases, Alzheimer disease, graft-versus-host disease, spontaneous abortion and allograft rejection. Preferred autoimmune diseases and inflammatory disorders (AIDs) are type-1 diabetes, multiple sclerosis, systemic lupus erythematous, and rheumatoid arthritis.

The liquid pharmaceutical composition of the invention is preferably administered by injection to the patient, for instance, by intravenous, intramuscular, intradermal or subcutaneous route. Preferred routes of administration are subcutaneous route and intradermal route. In a preferred embodiment, the liquid pharmaceutical composition of the invention is for subcutaneous injection.

The liquid pharmaceutical composition of the invention is preferably suitable to deliver a dose of Il-2 ranging from 0.1 MIU to 3 MIU of interleukine-2, such as a dose of 0.2, 0.3, 0.4, 0.5, 0.6, 0.7, 0.8, 0.9, 1.0, 1.5, 2.0, 2.5, or 3.0 MIU.

Accordingly, the liquid pharmaceutical composition of the invention may be for a use in the treatment or the prevention of an autoimmune, immune-related or inflammatory disorder, wherein said liquid pharmaceutical composition is administered by subcutaneous route so as to provide a dose of Il-2 from 0.1 MIU to 3 MIU to the patient.

The liquid pharmaceutical composition of the invention is suitable for frequent administrations. Typically, the liquid pharmaceutical composition of the invention can be administered once a month, once every two weeks, once a week, twice a week, or daily, depending on the disease to treat and the therapeutic effect to obtain. The treatment can last several days, several weeks, several months and even several years. The treatment can comprise an initiation course, wherein the liquid pharmaceutical composition of the invention is administered daily during several days, and a maintenance period wherein the liquid pharmaceutical composition of the invention is administered at a lower frequency, for instance once a month or once every two months.

In some embodiments, the liquid pharmaceutical composition of the invention is for a use in the treatment or the prevention of an autoimmune, immune-related or inflammatory disorder, wherein said composition is administered at least once a month.

In some additional or alternate embodiments, the liquid pharmaceutical composition of the invention is for a use in the long-term treatment of an autoimmune, immune-related or inflammatory disorder.

As used herein, "a long-term treatment" refers to a treatment lasting at least 3 months, wherein the liquid pharmaceutical composition of the invention is administered at least once a month.

The dose to administer, the frequency of administration, the schema of administration and the duration of the treatment will vary depending on the disorder to be treated or prevented, the gravity of the disorder, the characteristics of the patient, in particular the patient's age, weight, body surface area (BSA), general medical condition, medical history . . . .

The invention also relates to a method for the treatment or the prevention of an autoimmune, immune-related or inflammatory disorder, in a patient said method comprising administering the patient with a liquid pharmaceutical composition of the invention. As mentioned above, the liquid pharmaceutical composition is preferably administered by injection, in particular by subcutaneous route, in an amount corresponding to a dose of Il-2 ranging from 0.1 MIU to 3.0 MIU.

A further object of the invention is a device for injection, preferably for subcutaneous injection, filled with the liquid pharmaceutical composition of the invention. The device may be for instance a syringe or a pen. Preferably, the device is suitable to provide subcutaneous administration of the liquid pharmaceutical composition of the invention. The device may be adapted to provide a single dose or a multi-dose of the liquid pharmaceutical composition of the invention. Each dose of the liquid pharmaceutical composition of the invention preferably corresponds to an amount of IL-2 ranging from 0.1 MIU to 3.0 MIU. Typically, the device of the invention is suitable to deliver a volume ranging from 50 µl to 2 mL, preferably from 100 µl to 1 mL.

In some embodiment, the device of the invention is for a single use. The device is preferably disposable.

In some other embodiments, the device of the invention is adapted to deliver multi-dose, such as a multidose pens.

In some embodiment, the device contains means enabling to adjust the amount of the liquid pharmaceutical composition to administer. In alternate embodiments, the device is suitable to administer a fixed amount of the liquid pharmaceutical composition.

Preferably, the device is suitable for self-administration.

In some embodiments, the device of the invention can be a pre-filled syringe or a pre-filled cartridge which can be used with an auto-injector. The auto-injector can be electronic or mechanic.

Devices suitable for subcutaneous administration and/or self-administration are well-known from the prior art. Several hormonal products are sold in pre-filled pens or pre-filled syringes. For instance on can refer to devices used for the administration of insulin such as insulin pens (such as those marketed under the tradename NovoPen® by NovoNordisk) or insulin hypodermic syringes.

It goes without saying that hypodermic needles can be adapted on said syringes or pens for performing the injection.

As further examples, one can refer to the subcutaneous delivery systems marketed for the administration of Rebif® (INF-1a) such as Rebif® Rebidose, which is a single use, pre-filled pen, RebiSmart® which is an electronic autoinjection device designed for self-administration with multi-dose cartridge, and Rebiject II®, which is an auto-injector designed for self-administration with pre-filled syringe.

If the device of the invention is a syringe, such a syringe is preferably a preassembled syringe, this means that the needle is already mounted on the syringe. For instance, one can refer to the preassembled syringe of Orgalutran®.

In some alternate or additional embodiments, the syringe is adapted for a use with an autoinjector.

Preferably the device is a multidose pen or a glass syringe, for instance a 0.5 to 1.5 ml syringe. The syringe can be equipped with a cap or a needle recovered by a cap.

Other devices for self-injection can be used. For instance, on can use needle-free delivery devices adapted for subcutaneous administration such as Zeneo® marketed by Crossject. This system is based on the principle of a cutting jet water: a liquid jet confined within a glass capsule is forced out through an injection nozzle of very small diameter, with a velocity of 150 meters/second which is enough to pass through the tissues.

In another aspect, the invention relates to a kit containing:
- a vial or a cartridge comprising the liquid pharmaceutical compositions of the invention and
- means for administration such as syringe(s), needle(s) and/or autoinjector device(s).

The following examples are provided by way of illustration only and not by way of limitation.

EXAMPLES

Stability Study

This study aims at assessing the stability of several pharmaceutical compositions of IL2 active substance (aldesleukin) over 36 months at 5° C. and 12 months at 30° C./75% RH.

1. Preparation of the Liquid Pharmaceutical Compositions of the Invention

Solutions are prepared from sterile IL2 active substance (concentrated solution comprising 25 MIU/ml equivalent to 2 mg/mL of IL2) in aseptic conditions under flow laminar hood at room temperature. IL2 active substance is diluted and formulated according to the formulation table hereunder. Each composition (1 ml) was packed under nitrogen atmosphere in type 1 siliconised glass vials which are closed with Flurotec bromobutyl stoppers.

| N° | [IL2] MIU/ml (mg/ml) | SDS (mg/ml) | Weight ratio SDS/IL2 | Ratio SDS in mg/IL2 in MUI | Mannitol (mg/ml) | NaCl (mg/ml) | Phosphate buffer (mM) |
|---|---|---|---|---|---|---|---|
| 1 | 1 (0.080) | 0.180 | 2.25 | 0.18 | 50 | 0 | 10 |
| 2 | 1 (0.080) | 0.180 | 2.25 | 0.18 | 0 | 8.3 | 10 |
| 3 | 1 (0.080) | 0.018 | 0.225 | 0.018 | 0 | 8.3 | 10 |
| 4 | 2 (0.160) | 0.360 | 2.25 | 0.18 | 50 | 0 | 10 |
| 5 | 2 (0.160) | 0.360 | 2.25 | 0.18 | 0 | 8.3 | 10 |
| 6 | 2 (0.160) | 0.035 | 0.225 | 0.018 | 0 | 8.3 | 10 |

-continued

| N° | [IL2] MIU/ml (mg/ml) | SDS (mg/ml) | Weight ratio SDS/IL2 | Ratio SDS in mg/IL2 in MUI | Mannitol (mg/ml) | NaCl (mg/ml) | Phosphate buffer (mM) |
|---|---|---|---|---|---|---|---|
| 7 | 5 (0.40) | 0.088 | 0.22 | 0.018 | 0 | 8.3 | 10 |
| 8 | 10 (0.80) | 0.176 | 0.22 | 0.018 | 0 | 8.3 | 10 |
| 9 | 20 (1.6) | 0.352 | 0.22 | 0.018 | 0 | 8.3 | 10 |
| 10 | 5 (0.40) | 0.360 | 0.9 | 0.072 | 0 | 8.3 | 10 |

2. Stability Studies

The prepared compositions are stored in monitored chambers at 5° C. or 30° C./75% RH for 36 months. Each composition (1-10) was assessed for its stability at month 6. Further stability analysis will be performed up to 36 months of storage.

Stability was assessed through validated analytical methods, in particular by Reversed phase HPLC (RP-HPLC) to determine the purity of IL-2 substance and the potential formation of degradation products, and by a biological activity assay. The RP-HPLC was performed in the following conditions:

Stationary phase: C4 column, Jupiter C4 5 µm, 300 Å, 4.6×250 mm from Phenomenex.

Gradient: elution is performed in in a 30 minutes gradient of buffer B (formic acid 0.1% in acetonitrile) in buffer A (formic acid 0.1% in ultrapure water) as described below:

| Time (min) | Flow (ml/min) | % Mobile phase A | % Mobile phase B |
|---|---|---|---|
| 0 | 1 | 60 | 40 |
| 5.00 | 1 | 45 | 55 |
| 15.00 | 1 | 30 | 70 |
| 20.00 | 1 | 0 | 100 |
| 23.10 | 1 | 0 | 100 |
| 24.00 | 1 | 60 | 40 |
| 30.00 | 1 | 60 | 40 |

Retention time of IL-2 is 14.0-14-6 minutes.

The starting IL2 active substance at 1 MIU/ml is injected as quality control.

The biological activity of IL-2 is preferably determined by a cell-based assay performed on HT-2 cell line (clone A5E, ATCC® CRL-1841™) whose growth is dependent on IL-2. Cell growth in the presence of a range of test interleukin-2 product is compared with the growth recorded with IL-2 international standard (WHO 2nd International Standard for INTERLEUKIN 2 (Human, rDNA derived) NIBSC code: 86/500). Cell growth is measured after addition and conversion of [3-(4,5-dimethylthiazol-2-yl)-5-(3-carboxymethoxyphenyl)-2-(4-sulfophenyl)-2H-tetrazolium (inner salt, MTS) into formazan by active viable cells. Formazan concentration is then measured by spectrophotometry at 490 nm. This concentration is directly proportional to the number of viable cells present in the culture.

Results

The purity and the biological activity of IL-2 substance were assessed in each formulation and for each condition of storage at month 6.

The results are shown in the below tables:

| | Biological activity (MIU/ml) | | | RPHPLC (% purity) | |
|---|---|---|---|---|---|
| N° | t0 | t0 + 6 months | % of activity at 6 months | t0 | t0 + 6 months |
| After 6 months of storage at 5° C. | | | | | |
| 1 | 1.0 | 0.67 | 67% | 98% | 98% |
| 2 | 1.0 | 0.77 | 77% | 99% | 99% |
| 3 | 1.0 | NA | NA | 99% | NA |
| 4 | 2.0 | 1.44 | 72% | 99% | 99% |
| 5 | 2.0 | 1.47 | 74% | 99% | 99% |
| 6 | 2.0 | NA | NA | 99% | NA |
| 7 | 5.0 | 4.47 | 89% | 99% | 100% |
| 8 | 10.0 | 9.81 | 98% | 99% | 99% |
| 9 | 20.0 | 23.5 | 118% | 99% | 99% |
| 10 | 5.0 | 4.59 | 92% | 99% | 99% |
| After 6 months of storage at 30° C. | | | | | |
| 1 | 1.0 | 0.60 | 60% | 98% | 85% |
| 2 | 1.0 | 0.62 | 62% | 99% | 85% |
| 3 | 1.0 | NA | NA | 99% | NA |
| 4 | 2.0 | 1.4 | 70% | 99% | 86% |
| 5 | 2.0 | 1.33 | 67% | 99% | 83% |
| 6 | 2.0 | NA | NA | 99% | NA |
| 7 | 5.0 | 3.45 | 69% | 99% | 86% |
| 8 | 10.0 | 9.46 | 95% | 99% | 86% |
| 9 | 20.0 | 15.3 | 77% | 99% | 88% |
| 10 | 5.0 | 4.03 | 81% | 99% | 82% |

All the formulations tested showed a good stability after a storage of 6 months at 5° C., except formulations 3 and 6. Formulations 3 and 6 already displayed a massive degradation of IL-2 after 3 months of storage at 5° C. and 30° C. After a storage of 3 months at 30° C., the percentage of residual biological activity was about 12% and 46% for formulations 3 and 6, respectively. This low stability may result from the low concentration of SDS in solution. It seems that a concentration of SDS of at least 0.05 mg/ml may be required to promote stability of IL2 in solution. To that respect, formulation 7 which contains 0.088 mg/ml of SDS exhibited a good stability at 5° C. and 30° C.

Noteworthy, formulations 7, 8 and 10 comprising from 5 to 10 MUI/ml of IL2 showed a good stability profile. The best results in terms of purity and biological activity after 6 months of storage at 5° C. and at 30° C. were obtained with formulation 8. Formulation 8 contains 10 MUI/ml of IL2, and 0.176 mg/ml of SDS with a weight ratio SDS/IL2 of 0.22. Formulations 1 and 4 are comparative formulations containing mannitol. Formulations 1 and 4 showed a similar stability in terms of purity and biological activity as Formulations 2 and 5 which are devoid of mannitol. Thus, the presence of mannitol is not needed to promote the stability of IL2 during the storage.

The invention claimed is:
1. A liquid pharmaceutical composition ready for injection to a patient, consisting essentially of:

(i) a non-lyophilized interleukin-2 having a specific activity of 8 to 18 MIU/mg of protein, which is present at a concentration of 0.1 to 20 million IU/mL (MIU/mL), (ii) a buffering agent at a concentration from 5 mM to 25 mM, wherein the buffering agent is selected from the group consisting of phosphoric acid, Tris(hydroxymethyl)aminomethane hydrochloride (TRIS-HCl), TRIS-glycine, citrate, borate, citrate/phosphate, bicarbonate, glutaric acid, succinic acid, salts thereof, and combinations thereof, and (iii) a surfactant at a concentration from 0.05 to 5 mg/mL, wherein the surfactant is selected from the group consisting of $C_8$-$C_{20}$ alkylsulfate salts, lauroyl sarcosinate salts, cholate salts, deoxycholate salts, and combinations thereof, in water.

2. The liquid pharmaceutical composition of claim 1, wherein the interleukin-2 is present at a concentration of 2 to 12 MIU/ml.

3. The liquid pharmaceutical composition of claim 1, wherein the surfactant is a $C_8$-$C_{20}$ alkylsulfate salt selected from the group consisting of an alkali metal salt of dodecyl sulphate and an alkaline-earth metal salt of dodecyl sulphate.

4. The liquid pharmaceutical composition of claim 1, wherein the surfactant is present at a concentration of 0.05 to 0.5 mg/mL.

5. The liquid pharmaceutical composition of claim 1, wherein the weight ratio of the surfactant to interleukin-2 is from 0.04 to 5.0.

6. The liquid pharmaceutical composition of claim 1, wherein the interleukin-2 is human interleukin-2 or aldesleukin.

7. The liquid pharmaceutical composition of claim 1, which is devoid of mannitol and/or albumin.

8. The liquid pharmaceutical composition according to claim 1, consisting essentially of a non-lyophilized interleukin-2 at a concentration of 2 to 12 MIU/mL, sodium dodecyl sulfate (SDS) at a concentration of about 0.05 to 0.5 mg/mL, a buffer selected from monobasic sodium phosphate, dibasic sodium phosphate and combinations thereof present at a concentration ranging from 5 mM to 25 mM, water, and optionally an osmolarity adjusting agent.

9. The liquid pharmaceutical composition according to claim 1, which is characterized by at least one of the following features:

the pH of the composition is from 7.1 to 7.8, the buffering agent is a phosphate buffer, interleukin-2 is aldesleukin, the weight ratio of the surfactant to IL-2 is from 0.1 to 3, the liquid pharmaceutical composition is suitable for a packaging in a delivery device for injection, the pharmaceutical composition is devoid of any lyophilization stabilizer, and/or the liquid pharmaceutical composition is stable at 5° C. for at least 6 months.

10. The liquid pharmaceutical composition according to claim 1, which is suitable for subcutaneous injection.

11. A pharmaceutical kit comprising a vial or a cartridge comprising the liquid composition as defined in claim 1, and means for subcutaneous injection.

12. The liquid pharmaceutical composition of claim 1, which is contained in a delivery system for subcutaneous injection.

13. The liquid pharmaceutical composition of claim 1, further comprising an excipient selected from the group consisting of antioxidants, osmolarity adjusting agents and preservatives.

14. The liquid pharmaceutical composition of claim 1, wherein the surfactant is sodium dodecyl sulfate (SDS) or lithium dodecyl sulfate.

15. The liquid pharmaceutical composition of claim 1, wherein the weight ratio of the surfactant to interleukin-2 is from 0.1 to 3.0.

16. The liquid pharmaceutical composition of claim 8, wherein the interleukin-2 is present at a concentration of 4 to 10 MIU/ml.

17. The liquid pharmaceutical composition of claim 8, wherein the interleukin-2 has a specific activity of 12±3 MIU/mg of protein.

* * * * *